(12) United States Patent
Loboda

(10) Patent No.: US 6,744,043 B2
(45) Date of Patent: Jun. 1, 2004

(54) ION MOBILTY SPECTROMETER INCORPORATING AN ION GUIDE IN COMBINATION WITH AN MS DEVICE

(75) Inventor: Alexander V. Loboda, North York (CA)

(73) Assignee: MDS Inc., Concord (CA)

( * ) Notice: Subject to any disclaimer, the term of this patent is extended or adjusted under 35 U.S.C. 154(b) by 0 days.

(21) Appl. No.: 10/004,800

(22) Filed: Dec. 7, 2001

(65) Prior Publication Data

US 2002/0070338 A1 Jun. 13, 2002

Related U.S. Application Data

(60) Provisional application No. 60/251,844, filed on Dec. 8, 2000.

(51) Int. Cl.[7] ............................................... H01J 49/40
(52) U.S. Cl. ...................... 250/287; 250/282; 250/292
(58) Field of Search ................................. 250/287, 282, 250/292, 396

(56) References Cited

U.S. PATENT DOCUMENTS

| | | | | |
|---|---|---|---|---|
| 5,572,035 A | * | 11/1996 | Franzen ....................... | 250/396 |
| 6,107,628 A | * | 8/2000 | Smith et al. ................. | 250/292 |
| 6,111,250 A | * | 8/2000 | Thomson et al. ........... | 250/282 |
| 6,323,482 B1 | * | 11/2001 | Clemmer et al. ........... | 250/287 |
| 6,331,702 B1 | | 12/2001 | Krutchinsky et al. | |

OTHER PUBLICATIONS

High Sensitivity Collisonally–activated Decomposition Tandem Mass Spectrometry on a Novel Quadrupole/orthogonal–acceleration Time–of–Fight Mass Spectrometer, Howard R. Morris, Thanai Paxton, Anne Dell, Jean Langhorne, Matthias Berg, Robert S. Bordoli, John Hoyes and Robert H. Bateman, *Rapid Communications in Mass Spectromerty*, vol. 10, pp. 889–896 (1996).

Rapid 'De Novo'Peptide Sequencing by a Combination of naoelectrorspray, Isotopic Labelling and a Quardrupole/ Time–of–fight Mass Spectrometer, Andrej Shevchenki, Igor Chernushevich, Werner Ens, Kenneth G. Standing, Bruce Thomson, Matthias Wilm and Matthias Mann, *Rapid Communications in Mass Spectrometry*, vol. 11, pp. 1015–1025 (1997).

Electrospray Ionization High–Field Asymmetric Waveform Ion Mobilty Spectrometry — Mass spectrometry, *Analytical Chemisty*, 1999, 71, 2346–2357.

Tandem Maldi–TOF–o–TOF MS with Collisonal Damping, Anatoli Verntchikov, Kevin Hayden and Marvin Vestal, Extended abstracts of ASMS–2000.

(List continued on next page.)

*Primary Examiner*—John R. Lee
*Assistant Examiner*—James J. Leybourne
(74) *Attorney, Agent, or Firm*—Bereskin & Parr

(57) ABSTRACT

A hybrid mass spectrometer comprises an ion mobility (IMS) section and a mass analysis section that analyses ions based on mass-to-charge ratios. In the IMS section, a DC potential gradient is established and a drift gas provided, so as to separate ions based on varying ion mobilities. Additionally, at least a downstream portion of the IMS section includes a rod set focusing ions along the axis, this prevents loss of ions and gives good transfer of ions into-a-mass analysis section, which can be a time-of-flight mass analyzer or an analyzer including a quadrupole rod set. A collision cell and mass analyzer can be provided between the two sections for MS/MS analysis. The IMS section then provides better utilization of an available sample; as each group of ions is elected from the IMS section, one ion can be mass selected as a precursor, for subsequent fragmentation/reaction and subsequent mass analysis of the product ions. Another aspect of the invention provides the ability to form potential wells, utilizing a segmented rod set configuration, so as to trap and hold ions after separation based on mobility characteristics.

43 Claims, 5 Drawing Sheets

OTHER PUBLICATIONS

A.N. Krutchinsky, A.V. Loboda, V.L. Spicer, R. Sworschak, W. Ens and K.G. Standing, Orthofonal Inection of Matrix–assisted Laser Desorption/Ionization Ions into a Time–of–fight Spectrometer Through a Collisonal Damping Interface, Rapid Communications in Mass Spectrometry, 1988, 50–518, vol. 12, John Wiley & Sons, Ltd.*

A.N. Krutchinsky, A.V. Loboda, V.L. Spicer, R Sworschak, W. Ens and K.G. Standing, Collsional Damping Interface for and Electrospray Ionization Time–of–Fight Mass Spectrometer, American Society for Mass Spectrometry, 1998, 569–579, vol. 9, Elsevier Science Inc.*

* cited by examiner

ION MOBILTY SPECTROMETER INCORPORATING AN ION GUIDE IN COMBINATION WITH AN MS DEVICE

This application claims benefit of provisional application No. 60/251,844, filed Dec. 8, 2000.

FIELD OF THE INVENTION

This invention relates to mass spectrometry and ion mobility spectrometry, and more particularly is concerned with a hybrid mobility-mass spectrometry apparatus and a new method of using such a hybrid device.

BACKGROUND OF THE INVENTION

Presently, there are a wide variety of different analysis techniques known for analyzing solvents and substances of interest.

Fundamentally, all mass analysis instruments operate at low pressures, at least in the mass analysis section. As such, separation of different ions depends solely upon different mass-to-charge ratios of the ions present. A problem thus arises where one has two similar ions which happen to have an identical or similar mass-to-charge ratio. Such ions are considered to be isobaric, and cannot be separated by conventional mass spectrometry techniques.

Another known technique for analyzing substances is ion mobility spectrometry (IMS). In such a system, a substance to be analyzed is ionized, to the extent possible, as is required of the low pressure mass spectrometry technique detailed above; however, the techniques for ionization unnecessarily differ due to the different pressures and operating conditions. IMS is commonly carried out at higher pressures, even at atmospheric pressure, and can even use ambient air. However, it is often preferred to use some known, selected gas which is dry, clean and pure and has known properties. Ions are then caused to travel down a drift tube under a potential gradient, through the gas. Different ions have different mobility characteristics depending upon the size and type of the ion and its charge. Thus, different ions will have different transit times to traverse the drift tube. Ions are detected at a detector at an exit from the drift tube, and, knowing transit times for different ions, the constituent components of a sample can be determined.

A drawback with IMS is that it can provide only poor resolution (approximately 100 for example) as compared to other known mass spectrometers. The problem is related to diffusion of the gas in the drift tube. In contrast, the low pressure mass spectrometry techniques detailed above can provide high resolution (for example, approximately 10000) and consequently can distinguish between ions having close but different mass-to-charge ratios.

Again, there is a problem with IMS techniques in that one can encounter substances that have similar drift times but are in fact quite different. Such substances cannot be resolved or separated by IMS.

There are also other known separation techniques relying on quite different technologies, such as chromatography and electrophoresis. For example, liquid chromatography involves passing a sample in a liquid phase through a chromatography column. The column is provided with a packing, selected to provide different retention properties for substances of interest. Then, by analyzing substances as they leave the chromatography column and measuring the time taken to traverse the column, an initial sample can be broken down into its separate portions.

Another known separation technique, electrophoresis, in turn relies upon the fact that different ions will have different mobilities in a liquid phase. A DC voltage or potential gradient is applied to a column, typically made of a liquid or gel, and a starting substance or sample to be analyzed is injected at the entrance end of the electrophoresis column. The potential gradient causes different components of the sample to traverse through the gel at different rates, due to their different mobilities. Again, this enables different components to be detected as they leave the electrophoresis column. Alternatively, at some point the potential gradient can be turned off, so as to fix the different components at different physical locations within the gel, which then can be physically broken into separate portions for analysis.

Accordingly, it has been recognized by a number of workers in this field that there is some advantage in providing so called two-dimensional separation techniques. In liquid chromatography and electrophoresis, there have been proposals which involve taking a sample, subjecting it to a first separation technique and then another separation technique of the same type. For example, in electrophoresis, a sample can be subjected to electrophoresis separation in a gel of one type, and then a second electrophoresis separation step in a second gel having different characteristics, intended to separate out any constituents present which may have had identical characteristics in the first gel.

Such separation techniques are often considered to be "orthogonal", since the two separation steps are wholly independent of one another. Moreover, the results can be presented as a two-dimensional chart, with orthogonal axes, where each axis represents one of the separation steps.

Moreover, there has been a proposal for combining quite different separation techniques. For instance, there has been a proposal to combine liquid chromatography or electrophoresis with some type of mass spectrometry. This can present a number of difficulties.

Firstly, a sample from liquid chromatography or electrophoresis has to be processed so as to be in a form suitable for generation of ions from mass spectrometry. For example, many modern mass spectrometers use an electrospray technique. The sample thus has to be introduced to an electrospray source, while maintaining any resolution obtained from the previous electrophoresis separation technique or the like. Earlier PCT patent application No. PCT/CA99/00868 demonstrates one proposal for such a technique.

Another fundamental problem is that the sample in capillary electrophoresis or liquid chromatography is carried out in a buffer. Once the sample is electrosprayed the mass spectrum will feature peaks related to the sample and also a wide range of peaks related to the buffer. These buffer related peaks are commonly called "chemical noise". It is the chemical noise that often imposes limits on the detection of the minute amounts of sample. Additionally, techniques such as electrophoresis are labor intensive as a gel has to be prepared for each run.

SUMMARY OF THE PRESENT INVENTION

Low pressure mass spectrometry, which inherently depends solely on the mass-to-charge characteristics of each ion, and ion mobility spectrometry (IMS) have been considered to be two different but similar techniques. They are considerably different, since they inherently rely on different techniques to achieve separation. At the same time, there are significant similarities; IMS relies on different mobilities of ions in a gas phase; low pressure mass spectrometry while, ideally, taking place in an absolute vacuum, necessarily has some gas pressure present, and additional steps, such as collisional fragmentation, inherently require the presence of a significant gas pressure thereby providing some, superficial similarity with IMS.

U.S. Pat. No. 5,905,258 (Clemmer) discloses a Hybrid ion mobility and mass spectrometer and there have been other proposals for a hybrid spectrometer (Fuhrer et al. Anal. Chem. 2000, 72, 3965–3971). These proposals recognize that there are significant advantages in combining an IMS technique with a low pressure mass spectrometry technique. Such hybrid instruments provide the advantages of two different separation techniques, thereby enabling separation of two or more constituents or ions which, in either one of the techniques, have similar characteristics preventing separation.

The ion mobility step can be operated at a pressure much less than atmospheric pressure, so as to enable it to be fairly readily combined with a low pressure MS technique, without imposing any undue requirements with respect to pumping or maintaining separation between different chambers and the like. The main problem of a low pressure mobility separation setup is in the resultant high rate of diffusion. Losses of the ions occur when the diameter of the ion beam becomes bigger than the diameter acceptable for mass spectrometer. It has been proposed to use a multipole ion guide with an axial field to overcome the diffusion problem in U.S. Pat. No. 5,847,386. The multipole ion guide can confine the ion beam and even reduce the beam diameter so that it will become acceptable for mass analysis.

One aspect of the present invention is to provide an ion mobility spectrometer having a rod set to promote confinement of the ions to the axis. The DC draft field or gradient can be provided in many ways. It is preferably provided by forming the rod set as a segmented rod structure. The individual segments of each rod can then be provided with a differing DC potential to establish the potential gradient.

In accordance with another aspect of the present invention, there is provided a spectrometer comprising: an ion mobility spectrometer (IMS) device, for use in promoting separation of ions based on different mobility characteristics, the ion mobility spectrometer device comprising: an inlet for ions; a rod set having an axis and comprising a plurality of individual rods arranged around an axis; means for applying an RF voltage to the rod segments for focusing ions along the axis; and means for forming a DC field within the rod set, to generate a potential gradient along the device;

and means for maintaining a gas pressure within the rod set whereby ions travelling through the rod set under the influence of potential gradient are subject to collision with the gas, promoting separation based on differing mobility characteristics; and at least one mass analysis section, providing a first mass analysis section, for receiving ions from the ion mobility spectrometer device and for separating ions based on differing mass-to-charge characteristics.

As mentioned, segmented rods can be provided. Alternatively, the means for forming the DC field comprises one of: auxiliary elements located around the rod set and connected to a power supply for generating the DC field and the potential gradient; and providing the rods of the rod set with inclined surfaces whereby a potential gradient can be formed.

The IMS section can include an upstream ring guide section where the pressure is relatively high, as focusing of ions with a rod set is poor at high pressures.

The mass analysis section can comprise a time-of-flight mass analyzer or a quadrupole rod set with a detector, for example. Additionally, for MS/MS analysis, a collision cell and a second mass analyzer can be provided.

Another aspect of the present invention provides a method of separating ions based on ion mobility characteristics, the method comprising:

(i) generating ions;
(ii) providing a drift region having an axis extending therealong and providing a rod set having a plurality of rod segments, with the drift region being located within the rod set, and maintaining a gas at a desired pressure in the drift region;
(iii) applying an RF voltage to the rod set to maintain desired ions focused along the axis of the rod set; forming a DC potential gradient along the rod segments of the rod set;
(iv) supplying ions to the drift region, whereby ions are driven through the drift region by the potential gradient and ions tend to separate due to differing ion mobility characteristics, and
(v) passing ions into a mass analyzer for mass analysis in dependence upon ion mass-to-charge ratios.

Preferably, the method includes separating ions into groups of ions in step (iv) in dependence upon ion mobility characteristics, and sequentially analyzing each group of ions in step (v).

More preferably, the method includes establishing for each group of ions an approximate range of mass-to-charge ratios present in the group, and mass analyzing the ions in step (v) in a Time-of-Flight mass analyzer, and setting timing of the Time-of-Flight mass analyzer in dependence upon the range of mass-to-charge ratios present in each group, thereby to enhance the sensitivity of mass analysis in the Time-of-Flight mass analyzer.

Another aspect of the method includes, between steps (iv) and (v), passing the ions through a collision cell to promote formation of product ions; by one of fragmentation and reaction, and subsequently mass analyzing the product ions in step (v).

More preferably, before passing the ions into the collision cell, the method includes subjecting the ions to an upstream mass analysis step, to select a desired precursor ion for said at least one of fragmentation and reaction, and periodically resetting the precursor ion selected in said upstream mass analysis step, as different ions pass out from step (iv), thereby to increase utilize usage of ions from a sample.

The present invention also provides for utilization of a segmented rod structure to form wells for trapping ions, after separating ions based on their mobility characteristics. Then the ions in each well can be separately released for mass analysis, collision and subsequent mass analysis, or any other purpose.

A further apparatus aspect of the present invention provides an apparatus comprising: an ion mobility spectrometer device, for use in promoting separation of ions based on different mobility characteristics, the ion mobility spectrometer device comprising an inlet for ions; a drift region; means for forming a DC field along the drift region, to generate a potential gradient along the drift region; and means for maintaining a gas pressure within the drift region, whereby ions travelling through the drift region under the influence of a potential gradient are subject to collision with a gas, promoting separation based on differing ion mobility characteristics;

a collision cell connected to the ion mobility spectrometer for receiving ions therefrom and including a gas therein, for promoting at least one of fragmentation of ions and reaction of the ions with ambient gas, to form product ions; and a final mass analysis section for analyzing the product ions.

The method aspect of the present invention also provides a method for separating ions based on ion mobility characteristics, the method comprising:

(i) generating ions;

(ii) providing a drift region having an axis extending there along;

(iii) forming a DC gradient along the drift region;

(iv) supplying ions to the drift region, whereby ions are driven through the drift region by the potential gradient, thereby to promote ion separation due to differing ion mobility characteristics;

(v) passing the ions into a collision cell to promote at least one of fragmentation and reaction with a collision gas, thereby to generate product ions;

(vi) subjecting the product ions to mass analysis.

Yet another aspect of the method of the present invention provides a method of operating a spectrometer system comprising an ion mobility section connected to a time-of-flight mass spectrometer, the method comprising;

(i) generating ions;

(ii) supplying the ions to the drift region of the IMS section;

(iii) forming a DC potential gradient along the drift region of the IMS section, thereby to promote separation of ions based on differing mobility characteristics;

(iv) supplying ions eluting from the ion mobility section to the time-of-flight mass spectrometer; and (v) adjusting the duty cycle of the time-of-flight mass spectrometer to correspond to the range of mass-to-charge ratios in each group of ions received from the ion mobility section, thereby to enhance the overall duty cycle of the time-of-flight spectrometer.

BRIEF DESCRIPTION OF THE DRAWING FIGURES

For a better understanding of the present invention and to show more clearly how it may be carried into effect, reference will now be made, by way of example, to the accompanying drawings, which show preferred embodiments of the present invention and in which.

DESCRIPTION OF THE PREFERRED EMBODIMENT

Figure 1:
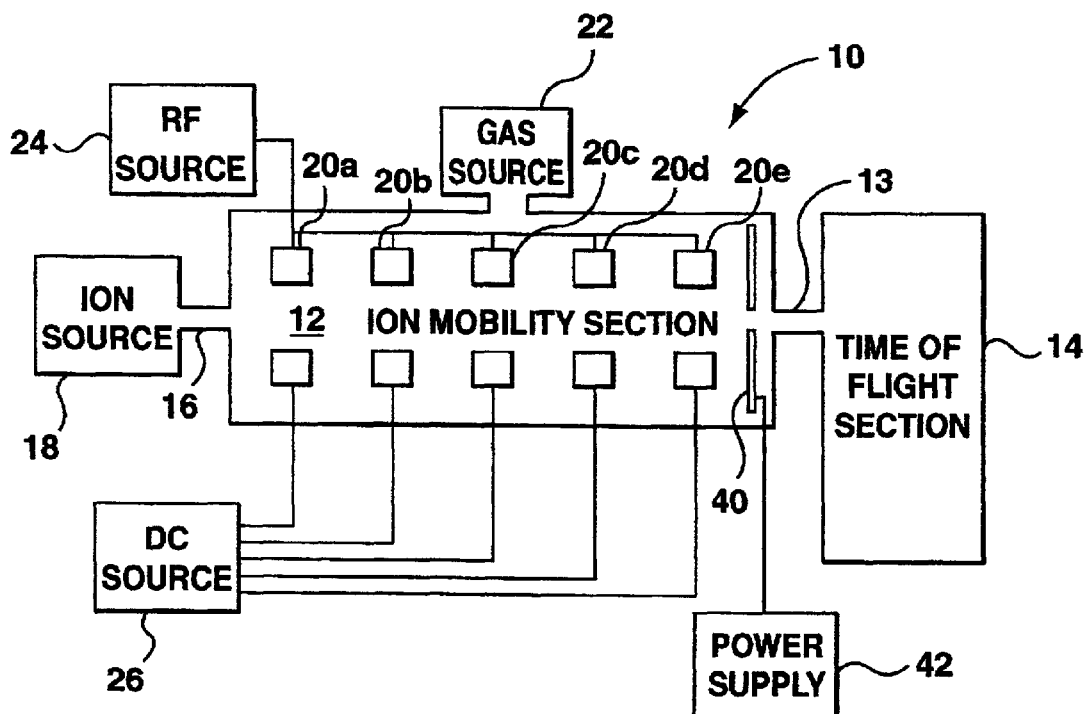
FIG. 1 is a schematic view of a first embodiment of a spectrometer apparatus in accordance with the invention.

Referring first to FIG. 1, there is shown a first embodiment of an apparatus indicated generally by the reference 10. The apparatus 10 includes an ion mobility section 12 and a time-of-flight section 14.

The ion mobility section 12 includes an input 16 for ions. Ions can be generated by any suitable ion source indicated schematically at 18. Pulsed ions sources like MALDI can be used here without any extra components, as they inherently produce pulses of ions as required for an IMS device. For continuous sources like electrospray these can be used in combination with a converter for converting the continuous ion beam into the pulsed one. The converter can be represented by some kind of an ion accumulation device or trap, including pulse extraction capabilities, such as 2D or 3D ion traps, for example. The ion mobility section (IMS) 12 has a drift or mobility section along its length, and is provided with a segmented quadrupole rod set indicated at 20, with each segment indicated as 20a, 20b, etc. It will be understood that each segment 20a, 20b, etc. comprises four elements of a quadrupole rod set, typically four short rods arranged in a square; it will equally be understood that hyperbolic shaped elements and the like can alternatively be used. The various segments 20a, 20b, etc. are aligned with one another. It will also be understood that the number of rod segments can be varied, as detailed below; also a stacked ring ion guide can be used for this purposes in a similar fashion. A source of gas is provided at 22 and is connected to the ion mobility section 12, for maintaining a desired pressure within the ion mobility section 12.

Unlike some known IMS techniques where high pressure, even as high as atmospheric pressure, are used, it is anticipated that pressures in the range of 50–100 mTorr, possibly up to 1 Torr will be used. A preferred gas is nitrogen, although any suitable gas can be used. Additionally, it is anticipated that 10 Torr may represent an absolute upper limit for operation of the ion guide with an axial field as an IMS. The pressure of 10 Torr represents an upper limit of the RF ion guide operation, as above this pressure the effect of ion confinement weakens and disappears. Thus, for this purpose, pumps would be provided (not shown) for maintaining the desired sub-atmospheric pressure in the ion mobility section 12.

Figure 1A:
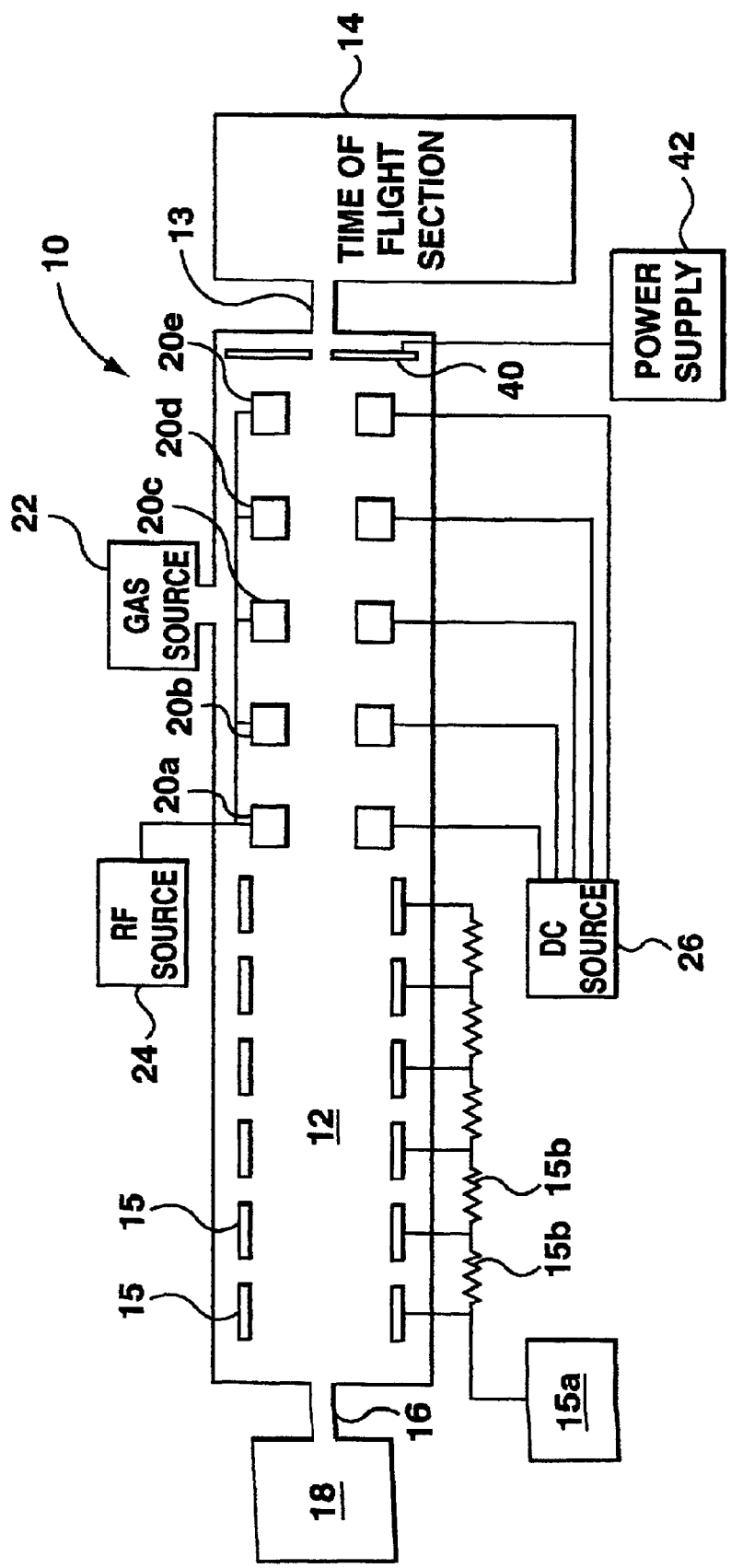
FIG. 1a shows schematically a variant of the first embodiment of the apparatus, including a ring guide.

FIG. 1a is shows a variant of the first embodiment of a spectrometer apparatus, in which a set of rings 15 is provided between the ion source 18 and the segmented quadrupole rod set 20. A corresponding DC voltage source 15a supplies power through resistor 15b to the rings 15. The pressure in the area of the ring set can be much higher than the one in the segmented quadrupole, for example 100 Torr or even up to 1 Atm. It is easier to achieve higher mobility resolution in a setup with higher pressure. Thus, the ions can be separated in the set of rings, and then passed through an orifice to the quadrupole rod set maintained at a lower pressure. Figure 1a shows a continuous chamber containing the rings 15 and the quadrupole rod set 20, but it will be understood that, where substantially different pressures are to be maintained for the rings 15 and the rod set 20, then some form of a barrier with an orifice for the ion flow is provided. The quadrupole rod set 20 then mainly serves to improve the beam quality, i.e. focussing along the axis, while preserving the mobility resolution in the axial direction.

The present invention also recognizes that the RF signal applied to the rod set 20 should be varied to track changes in the m/z ratio of ions eluted from the drift region. Thus, frequency and amplitude can be varied. For light ions a low RF voltage is required, while for heavier ions a larger RF voltage is desirable to give better focusing.

Figure 2:
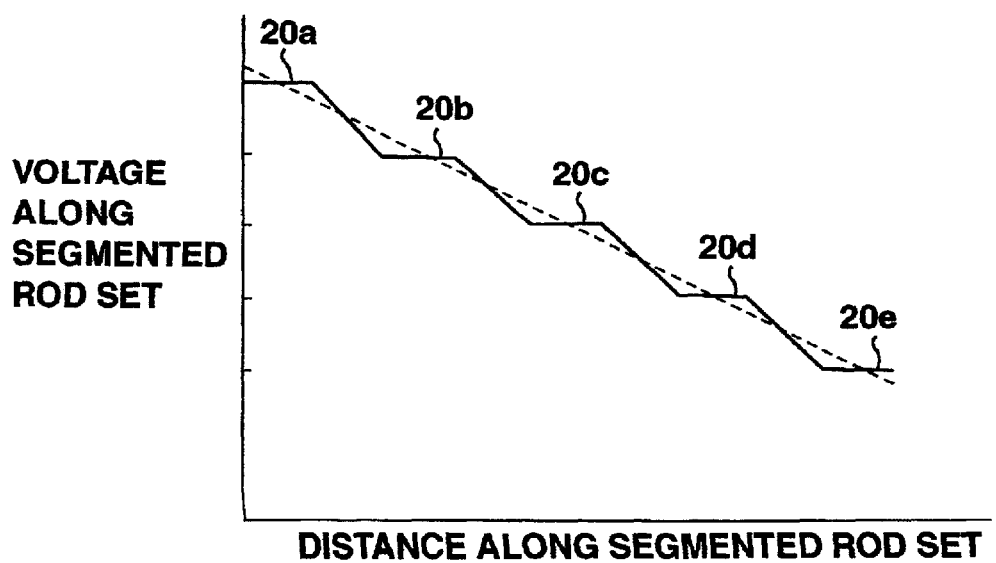
FIG. 2 is the voltage profile seen across the segmented rod set of FIG. 1.

For guiding the ions, a first RF source 24 is connected to the rod set 20, for providing an RF voltage. With an RF voltage, the rod set 20 operates as an ion guide and will transmit all masses up to a certain maximum mass set by the parameters of the applied RF voltage. Additionally, to drive ions through the IMS section 12, a DC voltage source 26 is provided, connected to each of the segments 20a, 20b, etc. individually or in series. This enables a voltage profile to be provided along the rod set as indicated in FIG. 2, with a voltage at each rod set indicated separately. The potential gradient provided along the rod set 20 is thus not strictly linear, but it will serve to maintain a substantial constant velocity for ions. This will cause each ion to reach some average velocity that is balanced by the drag of the gas in the IMS section 12. As mentioned, each ion will have its own characteristic drift velocity, and hence drift time, through the IMS section 12.

Figure 3:
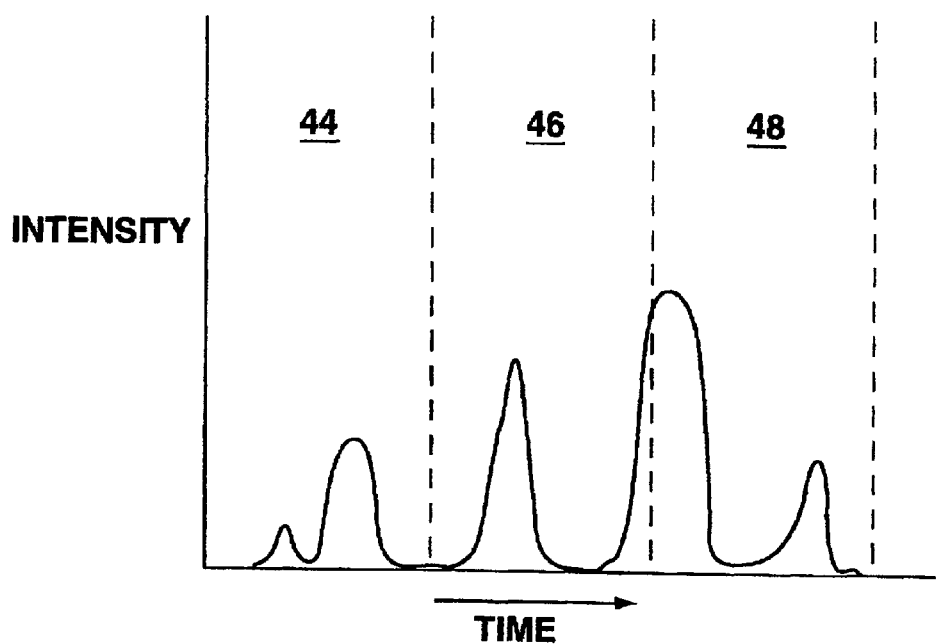
FIG. 3 is an arbitrary spectrum of an input sample.

Thus, on leaving the IMS section 12, an input sample will appear as a series of peaks of varying intensity at different times, as indicated in FIG. 3, which show a purely arbitrary spectrum.

Figure 4:
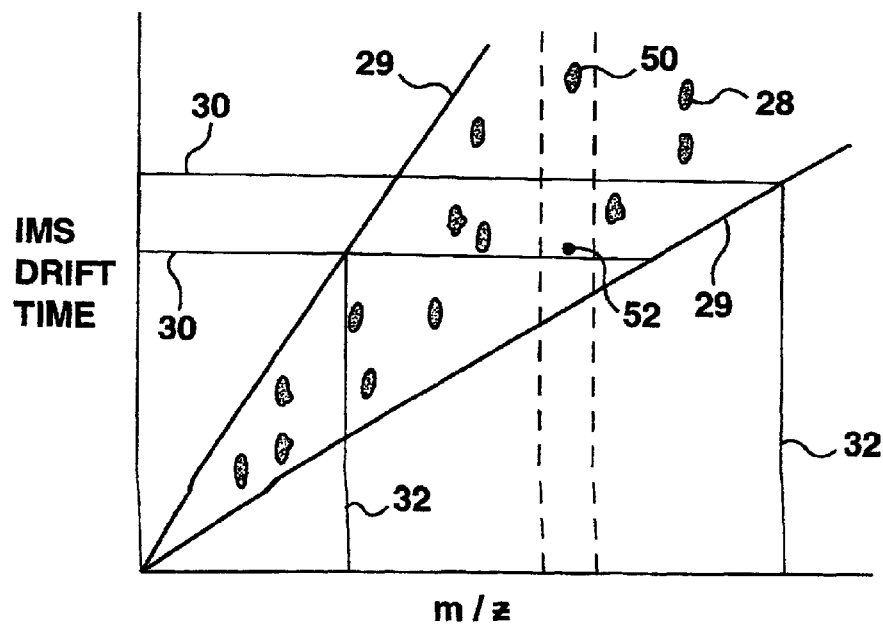
FIG. 4 is a graph showing variation of IMS drift time with mass-to-charge ratio.

Now, one of the key realizations made by the present inventor is that, while the separation technique provided by an IMS device and a low pressure mass spectrometer are inherently different, there is often some approximate correspondence between an ion's behavior in the two separation techniques. Thus, a heavy ion which takes a long time to pass through a low pressure mass spectrometer due to a large mass-to-charge (m/z) ratio will, in general, also have a low mobility, resulting in a large drift or transit time through an IMS device. In some respects, this is not too surprising; the bigger the ions the higher the mass to charge ratio they typically have, while at the same time these bigger ions have a larger cross section and thus longer drift times. Clearly, there will be no exact correspondence, and indeed this is an advantage, since it enables separation of two different constituents, which have identical characteristics in one of the separation techniques but not in the other separation technique. FIG. 4 is a graph showing variation of IMS drift time with m/z ratio for typical substances. Exemplary points are indicated at 28, and diagonal lines 29 indicate the boundaries of the area where the different points 28 are located. This shows that, in general, there is a loose or approximate correspondence between increasing mass-to-charge ratio and increasing IMS drift time. Clearly, it must be recognized that this may not always be the case, and there will be exceptions, but in most situations, one will know the constituents that might be present and their individual characteristics, so that allowance can be made for any unusual combinations of m/z and IMS drift time.

Thus, a first aspect of the present invention is the realization, made by the inventor, that this characteristic of FIG. 4 can be used to improve the sensitivity of a TOF mass spectrometer. One of the disadvantages of the TOF mass spectrometer is that it inherently requires a pulsed or intermittent operation. Thus, once a pulse of ions has been injected into the TOF flight tube, one will necessarily wait until all of the ions in the sample have traveled the length of the flight tube and been detected, before injecting the next pulse. Where a sample of ions has a wide m/z ratio, this results in a poor duty cycle, since a long time period must be provided between pulses, to enable all ions to clear the drift tube; failure to do this, can result in late arriving ions from a previous pulse contaminating a reading taking for a second or later pulse and so on.

For instance, a typical duty cycle for an orthogonal injection TOF section can be 20–25%, or even as low as 5% for low masses. The duty cycle is the ratio of the number of ions that will be analyzed in the TOF section to the number of ions entering the TOF section.

Techniques have been attempted to overcome this difficulty, e.g. by providing ion trap or the like, to trap and store ions immediately upstream of the inlet of the TOF section [Lubman: Qian M., Lubman D.; *Anal. Chem.*, 67, 234A (1995), Mordehai, U.S. Pat. No. 5,569,917, Cotter: Doroshenko V., Cotter R.; *Journal of Mass Spectrometry*, V. 33, 305–318, (1998) and also U.S. Pat. No. 5,905,258 (Clemmer)]. However, these techniques can be complex and are not always very satisfactory. Conditions to achieve high trapping efficiency and high mass resolution are often contradictory, especially over a broad range of ions.

Referring to FIG. 4, horizontal lines 30 indicate, by way of example, time on the IMS drift time axis, at which the inlet to the TOF section 14 is opened and closed to admission of ions. In other words, ions with IMS drift times between the horizontal lines 30 are admitted. Vertical lines 32 then indicate the corresponding m/z ratios on the horizontal axis. In general, ions will be admitted into the TOF section 14 for a fixed period of time, corresponding to a fixed spacing between the lines 30. For any such fixed period of time, there will be a corresponding mass range, as indicated by the pair of vertical lines 32.

It is this characteristic which enables an improved duty cycle to be obtained. The ions admitted to the TOF section then have a limited mass range, and this knowledge can be used to control timing of the TOF section 14. Thus, knowing the heaviest ion, i.e. the ion with the largest m/z ratio, the drift time in the TOF section 14 can be set to allow the heaviest ions to clear the drift tube. At the end of this time, a fresh batch of ions can then be admitted to the TOF section 14. This should give a significant increase in duty cycle, as opposed to the situation where the TOF is scanned at a constant frequency corresponding to the heaviest ion in the sample.

A further possibility in accordance with the present invention is to provide an ion gate 40, as indicated in FIG. 1. This would be connected to a respective power supply 42, for setting the DC potential at the ion gate 40. In normal use, this potential will be set low (for positively charged ions) to enable ions to freely pass from the IMS section 12 to the TOF section 14.

Now, to improve the duty cycle, once a group of ions have been admitted to the TOF section 14, the voltage at the ion gate 40 can be increased so as to trap ions in the IMS section 12. The potential gradient in the IMS section 12 will still tend to cause ions to travel through the IMS section 12, causing the ions to bunch up or concentrate adjacent to ion gate 40.

The technique then enables bunches or groups of ions to be admitted to the TOF section 14 as they arrive from the IMS section 12. This pulsed operation scheme is similar to the one described, but unlike the ones described in the above patents can achieve duty cycle close to 100% over the broad range of ion masses due to upstream mobility separation. Indeed, bunching setup allows duty cycle to be close to 100% over a narrow mass range, but the mass range for a certain slice on mobility scale is narrow (see FIG. 3.). Thus, at first the light ions will be bunched, then the medium ions and then the heavier ions, all ions will be bunched and analyzed sequentially with the duty cycle close to 100%.

This is best understood by further reference to FIG. 3. FIG. 3 has vertical lines breaking the spectrum up into three bands 44, 46 and 48. The first band 44, with a smaller range of times, would arrive at the outlet of the IMS section 12 first. It would be admitted to the TOF section 14 for analysis, while ions in the second band would be retained by operation of the gate 40. The time taken for ions to travel through the TOF section 14 will correspond to the width of each of the bands 44, 46 and 48. Thus, once the first group of ions has cleared through the TOF section 14, ions in the second band 46 would be admitted to the TOF section 14 for analysis. Similarly, the third band of ions 48 would be admitted after the second band 46 has been analyzed in TOF section 14. As shown, the division in the bands can even bisect known peaks in the spectrum from the IMS section 12. This is not a problem, since all of the results from analysis in TOF section 14 are ultimately totaled to give the complete spectrum.

It will also be appreciated that the number of bands (44, 46 and 48) is entirely arbitrary, and will depend upon a particular application, the sample being analyzed, the mass range of interest, desirable resolutions and other factors.

It can be noted that the time frame in the IMS section 12 will be relatively large, and each peak may be of the order 0.1–1 ms wide, with the overall spectrum spanning 10–50 ms. In the TOF section 14, scans may be obtained every 100 $\mu$sec, so that 1–10 TOF pulses or scans may be required to capture one IMS peak. One should note that the time scales here are approximate, and they can be varied by the choice of instrument dimensions, voltages and type of ions under investigation.

Peak width in mobility analysis is determined by the diffusion. Thus, it seems to be advantageous to reduce the duration of the mobility separation by increasing the potential difference along the axis. Unfortunately, in low pressure mobility devices, the fields often approach the limit where ions start to fragment. Ion fragmentation can occur when the drift velocity of the ions approaches approximately the thermal velocity of the buffer gas. Consequently, ions which have higher mobility coefficients are likely to fragment first. Once these higher mobility ions, usually the lighter ions, leave the mobility section, one can increase the field strength so that the medium and heavy ions will be moving faster, but not fast enough for fragmentation. As the medium ions exit, the field can be increased even more.

In general it might be possible to create an axial field with a certain time profile optimizing the peak width for a wide range of ions, while at the same time ensuring that no ions are accelerated sufficiently to cause ion fragmentation.

With respect to the ion source 18, this could be any suitable ion source. For example, it could be a MALDI (matrix assisted laser desorption ionization) source ion, which inherently produces pulses of ions. Thus, as each pulse enters the IMS section 12, it will spread out to generate the spectrum of FIG. 3. Alternatively, ions can be generated by electrospray ionization and then trapped. The trapped ions can then be admitted in pulses, in a known manner, to enable the spectrum of FIG. 3 to be generated. An ion trap can operate at any convenient pressure suitable for trapping and pulsed extraction.

It can be noted that this technique provides an orthogonal, two-dimensional separation technique. That is ions are subjected to two separate and distinct separation techniques, which while similar in many respects will act differently on individual ions. This difference can be exploited to separate ions which otherwise might have similar or isobaric characteristics when subject to just one separation technique.

For example, some ions are isobaric when subject to low pressure mass spectrometry, in that they have identical m/z ratios. This is indicated schematically in FIG. 4 for ions 50 and 52. If these ions are passed just through the TOF section 14, there would be no way to distinguish between them. However, as FIG. 4 shows, they have different characteristics when subjected to IMS, as shown by their different IMS drift times. Thus, by suitably selecting the timing of admission of bands or groups of ions into the TOF section 14, from the ion mobility section 12, these ions 50, 52 can be distinguished.

Correspondingly, there may be ions which would have similar IMS drift times, but which would have quite different m/z ratios, enabling them to be distinguished in the TOF section 14.

By these means, it is expected that it should be possible to separate and identify most of the different constituents of a sample. As noted above, this effectively gives a two-dimensional, orthogonal separation technique somewhat analogous to other two-dimensional separation techniques, such as capillary electrophoresis or liquid chromatography and conventional mass spectrometry. Unlike capillary electrophoresis and liquid chromatography, mobility separation doesn't add buffer ions to the overall spectrum. In fact, the opposite is true, the hybrid mobility-mass spectrometer can virtually clean up the ion beam contaminated with the buffer ions, since the buffer ions have significantly different structures from the ions of interest and their mobility separation can be very efficient. Thus, mobility-mass spectrometry can allow lower detection limits for ordinary samples as well as samples coming out of liquid chromatography or electrophoresis or other types of separation techniques.

Figure 5:
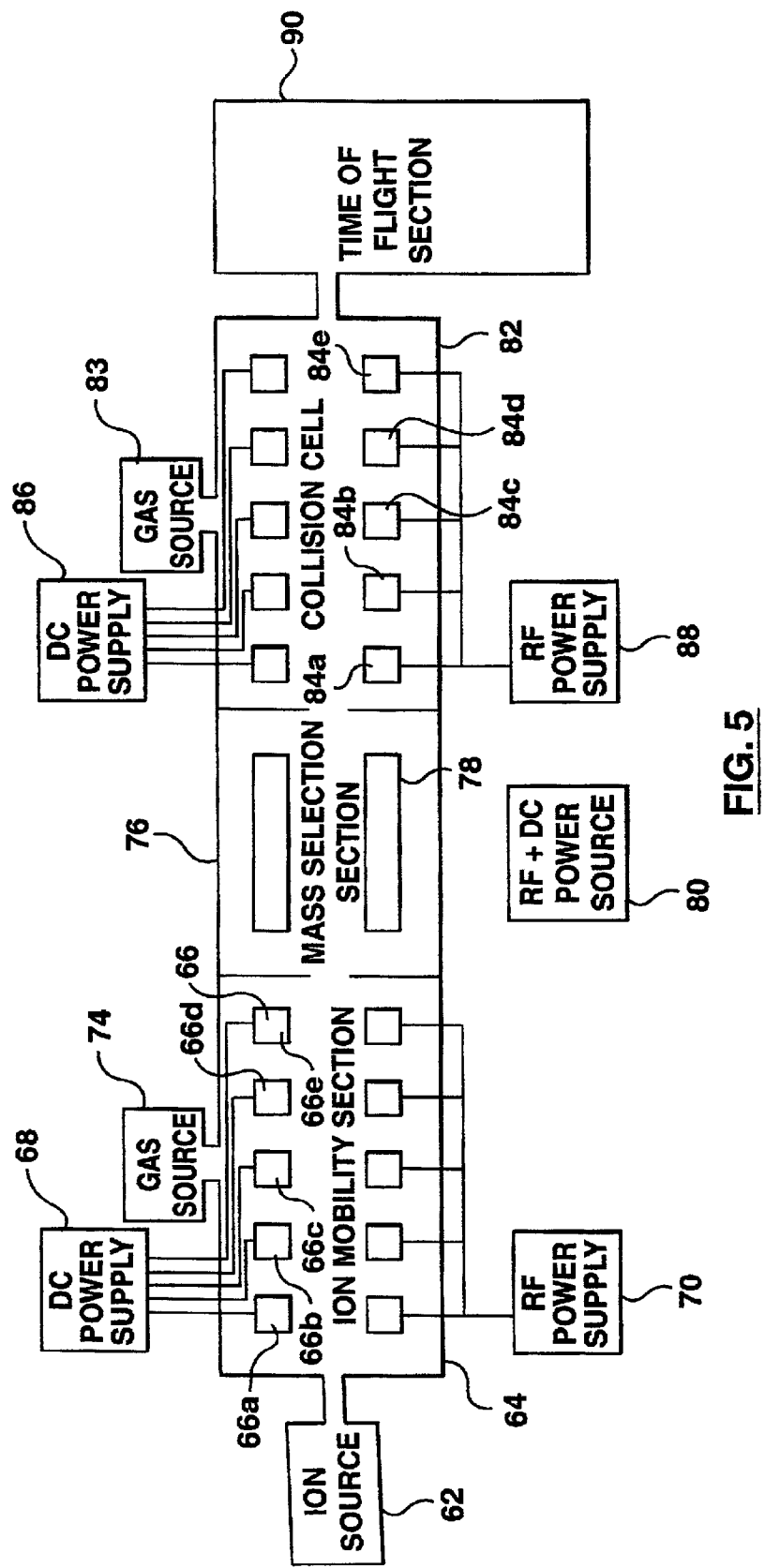
FIG. 5 is schematic view of a second embodiment of a spectrometer apparatus in accordance with the present invention.

Referring to FIG. 5, a second embodiment of the invention is shown and indicated generally by the reference 60. Here, an ion source 62 generates ions and the ions are admitted into an ion mobility section (IMS) 64, generally corresponding to the IMS section 12 of the first embodiment.

This IMS section 64 has a rod set 66, which again comprises a plurality rod segments 66a, 66b etc. The number of rod segments can vary, and for simplicity only a few are shown in FIG. 5. It is anticipated that the number of rod segments can be 10, 20, 60 or even higher. The length of the IMS section 64 can be varied as desired. Currently, the inventor is proposing an IMS section 64 that is 12 inches long, but a longer IMS section, for example 24 inches, would give better separation by the IMS technique.

A DC power supply 68 is connected to the various rod segments of the rod set 66, to generate a potential gradient, somewhat as shown in FIG. 2. Again, an RF power supply 70 is connected to the various segments of the rod set 66, for guiding and focusing ions through the ion mobility section 64.

A gas, for example nitrogen, is supplied from a gas source 74 to the IMS section 64. The IMS section 64 could be maintained at a pressure in the range of 1 m Torr to 10 Torr. The IMS section can be made as a two stage setup similar to the one depicted on FIG. 1a, in which case the pressure in the first mobility section can be up to 1 Atm.

From the IMS section 64, ions pass into a mass selection section 76, which here is shown including a quadrupole rod set 78. A power supply 80 is shown connected to the rod set 78. The power supply 80 can be a conventional RF and DC power supply for supplying a signal to the rod set, to select an ion with an m/z ratio of interest.

Downstream from the mass selection section 76, there is a collision cell 82. The collision cell includes a gas source 83, and pressure within the collision cell 82 can be controlled in known manner. The collision cell 82 has its own segmented rod set 84, which again includes a plurality of rod segments 84a, 84b etc. Use of a segmented rod set in this manner can follow that described in U.S. Pat. No. 5,847,386. It will also be understood by those skilled in the art that the collision cell could provide for surface induced dissociation.

Again, respective power supplies 86 and 88 are provided for a DC signal to establish a potential gradient through the rod set 84, and an RF field respectively. The power supply 88 can additionally supply some resolving DC component if it is desired to operate the collision cell in a band pass mode, as described in International Patent Application PCT/CA98/00536.

Finally, the collision cell 82 is connected to a TOF section 90. The TOF section 90 can be conventional, and details are not shown. In a known manner, it would include means for admitting ions, accelerating a selected group of ions into a drift tube and a detector at the end of the drift tube for detecting the ions and measuring the time-of-flight. An orthogonal TOF configuration is indicated in the drawing.

This arrangement of FIG. 5 is expected to provide an increased performance in MS/MS scans and the like. In effect, in addition to a first MS (mass selection) step, effecting in the mass selection section 76, ions are previously subjected to IMS separation in the IMS section 64. The second mass selection (MS) step occurs in the TOF section 90.

This can have the advantage of cleaning up a parent ion peak. Often, for a parent ion peak selected in the mass selection section 76, there will be various interfering peaks of ions that have similar, or even identical, m/z ratios. These cannot be distinguished by mass selection alone. The IMS section 64 thus has the advantage of enabling separation of these various interfering ions, by their different mobility characteristics. Thus, knowing both the m/z ratio of a parent ion and its mobility characteristics, the parent ions can be taken from the IMS section 64 at the appropriate time, with ions having lesser and greater mobilities being rejected. These parent ions are then subjected to further mass selection in section 76, which principally will ensure elimination of any ions which have accidentally been carried over and ions which have similar IMS characteristics but quite different m/z ratios.

Then, as is conventional, the selected parent ions will be passed into the collision cell 82 for fragmentation. As detailed in U.S. Pat. No. 5,847,386, the potential gradient maintained through the rod set 84 will ensure that the parent fragment ions travel through the collision cell 82 in a reasonable time, and no lengthy time will be needed to enable any "tail" allowance to clear from the collision cell 82. Additionally, the potential gradient maintains the velocity of the parent ions, to ensure good fragmentation efficiency. Thus, if any parent ions are subjected to glancing collisions, tending to reduce their kinetic energy without fragmenting the ions, they are then further accelerated until fragmentation does occur.

The fragment ions and any unfragmented parent ions then pass through to the TOF section 94 analysis of the fragments, again in known manner.

The arrangement or apparatus of FIG. 5 resembles a traditional tandem mass spectrometer, for example a quadrupole time of flight tandem mass QqTOF spectrometer. Such an instrument has several modes of operation as described in [Micromass paper: Morris H., Paxton T., Dell A., Langhorne J., Berg M., Bordoli R., Hoyes J., Bateman R.; *Rapid Commun. Mass Spectrom.*, 10, 889, (1996). Igor's paper: Shevchenko A., Chernushevich I., Spicer V., Ens W., Standing K., Thomson B., Wilm M., Mann M.; *Rapid Commun. Mass Spectrom.*, 1997, 11, 1015–1025]. An additional feature is that mobility separation allows one to increase sensitivity of such an instrument in different modes of operation. In the single MS mode (overall spectrum analysis) the sensitivity can be improved by using variable frequency scanning and/or bunching described above for the instrument FIG. 1 and FIG. 1a.

In MS/MS mode (fragment ion spectrum of a selected precursor) the sensitivity of the setup FIG. 5 can be further improved using parent ion multiplexing. Traditional QqTOF mass spectrometer can only select one precursor ion at a time, this represents a significant loss of sensitivity when analyzing mixtures containing more than one precursor ion of interest. Use of mobility separation in section 64 will produce a sequence of different precursor ions "eluting" out of the mobility stage. The quadrupole mass selector 76 can be tuned to the precursor ion of interest "eluting" at the moment. Thus, many precursor ions can be selected in the quadrupole 76, fragmented in the collision cell 82 and analyzed in the TOF 90 during the course of one experiment. This gives better use of a sample and does not require other precursors to be rejected while another precursor of interest is being analyzed.

It is to be noted that while capillary electrophoresis and chromatography have been used to give upstream separation, such techniques have various disadvantages, some of them described above. Also, the time scales are long, being in the order of seconds or minutes. In contrast, IMS gives time scales of the order of 10ths of milliseconds, so that typically there are only a few milliseconds to analyze each peak.

In MS/MS analysis, one of the key concerns is to get the best sensitivity. Accordingly, when using the technique of FIG. 5, it is desirable to ensure that all possible samples are collected and analyzed. To this end, some electronic equipment will be provided to switch between "eluting" peaks as described above. One can also temporarily stop the flow from the IMS section 64 to avoid waste of the adjacent peaks of interest. To this end, some sort of ion gate or the like can be provided. This enables "peak parking". As described above, this could simply be achieved by adjusting the voltages on a gate, to trap all these ions as required.

In some cases it may be advantageous to extend an analysis time for the "eluting" peak, this can be accomplished by reducing the potential difference along the IMS section 64. Additionally, when it is desired to empty ions from the IMS section 64, an increased voltage gradient can be provided. Consequently, when several mobility peaks need to be fragmented and analyzed the DC voltage along the mobility cell can be modulated by a certain function of time, so that the elution time of the peaks of interest is increased and the gaps or intervals between the peaks are reduced. It is to be noted that diffusion in the ion mobility section 64 depends upon the square root of the time in the mobility section 64, so that care has to be taken that peaks do not diffuse out to too great an extent.

A further aspect of the present invention is the realization that after separating ions into different groups, based on ion mobility, these ions can be held in individual wells. This setup can potentially give much higher analysis time for individual parent ions, when required. Conceptually, this borrows a technique from other separation technologies, such as gel electrophoresis. In gel electrophoresis, it is known to separate a sample into different groups, and then to turn off the applied field, effectively to freeze or hold different groups at different locations in the electrophoresis gel. This aspect of the invention is best understood by reference to FIG. 6 and FIGS. 7a–7d.

Figure 6:
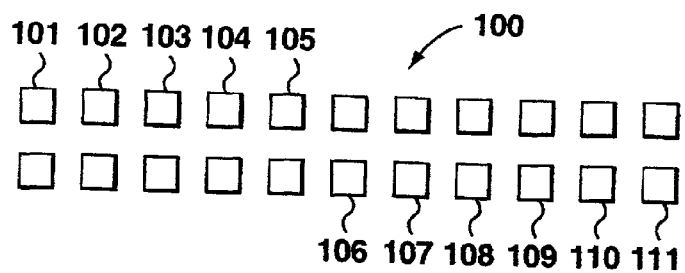
FIG. 6 is a diagrammatic view of an exemplary segmented rod set.

FIG. 6 shows an exemplary rod set indicated at 100, including a plurality of individual rod segments labeled 101, 102, through to 111. Although not shown in FIG. 6, this quadrupole rod set 100 would be located in an IMS section, supplied with suitable a gas, voltages etc., as described above in relation to FIG. 1 or FIG. 5. As for FIGS. 1 and 5, it would be supplied with RF and DC voltages.

Figure 7A:
FIG. 7a is one profile of the DC potential across the exemplary rod set of FIG. 6.
Figure 7B:
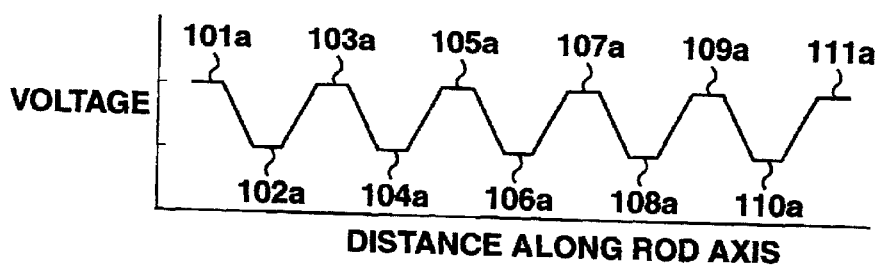
FIG. 7b is another profile of the DC potential across the exemplary rod set of FIG. 6 forming wells to store ions.
Figure 7C:
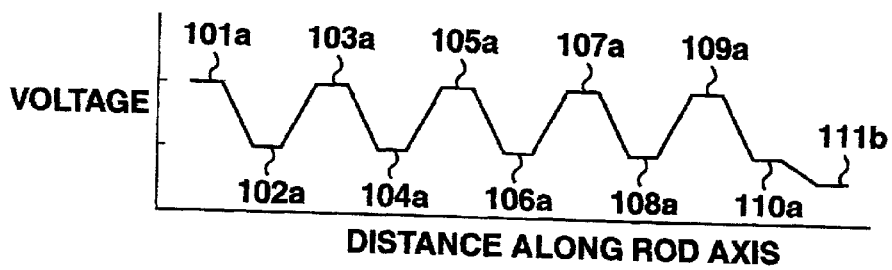
FIG. 7c is another profile of the DC potential across the exemplary rod set of FIG. 6 for emptying ions from one well.

In normal use for ion mobility separation, DC potentials would be applied to the different rod segments 101–111, so as to provide a small potential drop between each adjacent pair of rod segments. This would then generate the potential profile shown in FIG. 7a. (The potential profiles in FIGS. 7a, 7b and 7c are shown as comprising linear segments, but would in fact along the axis and away from the electrodes be more smoothly continuous, i.e. resembling a sine wave) Thus, through each rod set the potential is constant, and there is then an approximately uniform gradient down to the next rod set. This will ensure, to the extent possible, that ions are subject to a uniform gradient of field through the IMS section, promoting separation of ions based on ion mobility.

Now, in accordance with this aspect of the invention, once a sample of ions has been separated, so that the ions with the highest mobility are approaching the end of the rod set, around the rod segment 110, then the voltage source generating the field of FIG. 7a is turned off. Instead, voltages are applied to the segments 101–111, to generate the potential profile shown in FIG. 7b. All the odd numbered rod sets are provided with one, higher DC potential, while the even numbered rod sets 102, 104, 106 and 108 are provided with a lower DC potential with the new voltages indicated by the suffix 'a'. Then, in effect, a potential well is formed at each even numbered rod segment 102–108.

Simultaneously, the RF voltages applied to the rod set would be maintained, so as to keep ions focused along the axis of the overall rod set 100. This will then have the effect of causing ions to gather in the potential wells at the even numbered rod segments 102–110. These wells can alternatively be considered to be "micro vials".

Importantly, these wells or micro vials permit release of the ions in each well independently of the other ions. This is demonstrated in FIGS. 7c and 7d.

Thus, to release the ions around rod segment 110, the voltage 111a on the final rod segment 111 is dropped down to a lower voltage, as indicated at 111b in FIG. 7c. The DC voltages on the other rod segments 101–110 are maintained the same. This will cause the ions located at the first 4 potential wells at rod segment 102–108 to be retained. The ions at the rod segment 110 and 111 will then be subject to a potential gradient, tending to expel the ions towards the next element of the apparatus, e.g. the TOF 14 of FIG. 1 or the mass selection section 76 of FIG. 5. This enables this group or bunch of ions to be subject to further analysis in any suitable time frame. Once analysis of these ions is completed, then the next group or bunch of ions can be released.

Figure 7D:
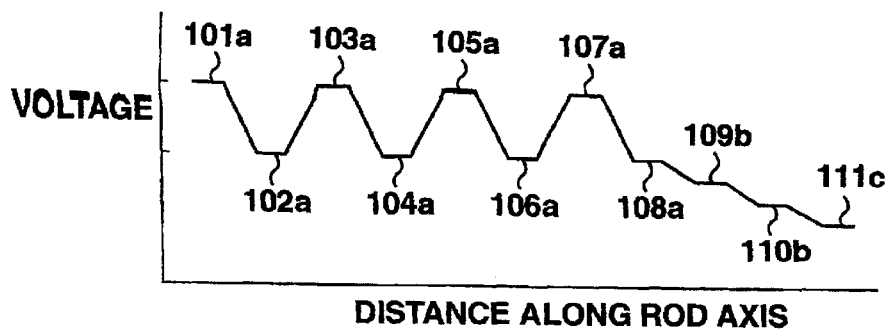
FIG. 7d is another profile of DC potential across the exemplary rod set of FIG. 6 for emptying ions from another well.

This is achieved by dropping the voltages on the rod segments 109 and 110 to voltages 109b and 110b, which are progressively lower than the voltage of 108a in FIG. 7d. Simultaneously the voltage at the rod segment 111 is dropped to an even lower voltage 111c. This will then give the progressive potential profile shown in FIG. 7d from the rod segment 108a, towards the exit of the IMS section. As for the previous group or bunch of ions, this then tends to drive the ions out of the IMS section into the next section for further processing.

It will be readily appreciated that this technique can be repeated for each of the remaining well at 102, 104 and 106, until all the ions have been progressively driven out of the IMS section and further analyzed.

The only anticipated problem is that if the ions are held for a long time, there may be excessive levels of reaction or interaction between the ions and the gas molecules. To avoid this, as soon as the potential well structure of FIG. 7b is formed, gas supplied to the IMS section can be turned off and the pressure can be pumped down to remove the gas. At low pressures, it is known that ions can be held for a significant period of time, over seconds, or even minutes. This potential well structure, combined with a focusing RF field should ensure that ions are stably retained within individual wells within the rod set 100.

It is expected that this technique will have particular application in a QqTOF instrument. In such an instrument, there is a first mass selection section (Q) for selection a parent ion, followed by a collision cell (q) for generating fragment ions, and a final TOF (Time of Flight) section for analyzing the fragments. A problem can arise with fragments tending to separate. The technique described above in relation to FIGS. 6 and 7 can be used to give better use of the sample for MS/MS analysis. For best effect, it is desirable to obtain a clean peak out of the IMS section.

As already pointed out above, the ions for the examples given can be from a variety of sources. For example, ions can be provided from: a MALDI source; an electrospray source; or any other suitable source. Also, ions entering IMS section can be preselected using different mass selection and other separation techniques. A few examples are provided below. MALDI ions can be preselected using time-of-flight separation and a pulsed gating similar to the one described in [Verentchikov: Verentchikov A., Hayden K., Vestal M.; "Tandem MALDI TOF-o-TOF MS with collisional damping"; Extended abstracts of ASMS-2000] before IMS section.

ESI ions can be preselected before entering IMS stage using capillary electrophoresis, liquid chromatography, FAIMS [Guevremont: Purves R., Guevremont R.; Analytical Chemistry, 1999, v13, p.2346–2357] or an ion trap.

It is also to be understood that while the described embodiments include quadrupole rod sets, for many purposes any suitable multipole rod set can be provided. In particular where no resolving characteristic is required then hexapole rod sets and the like can be used to provide the focussing function, to maintain ions close to the axis to prevent loss of ions from the device.

What is claimed is:

1. A spectrometer comprising:
    an ion mobility spectrometer (IMS) device, for use in promoting separation of ions based on different mobility characteristics, the ion mobility spectrometer device comprising:
    an inlet for ions;
    an ion mobility section for receiving ions from the ion inlet;
    means for forming an axial DC field within the pan mobility section, to generate a potential gradient along the axis thereof;

means for maintaining a gas at a desired pressure within the mobility section, whereby ions traveling through the mobility section under the influence of potential gradient are subject to collision with the gas, promoting separation based on differing mobility characteristics;

an ion focusing section including an RF ion guide having an axis, and means for supplying an RF voltage to the RF guide, to generate a field to promote focusing of ions along the axis of the RF ion guide, the ion mobility section being one of upstream from and internal with the ion focusing section; and at least one mass analysis section, providing a final mass analysis section, for receiving ions from the RF ion guide and for separating ions based on differing mass-to-charge characteristics.

2. A spectrometer as claimed in claim 1, wherein said means for maintaining a gas pressure comprises a gas supply, mounted for supplying gas to the mobility section, for maintaining a desired pressure in the mobility section.

3. A spectrometer as claimed in claim 1, which includes means for forming an axial DC field along the RF ion guide, to generate a potential gradient therealong to enhance movement of ions through the RF ion guide.

4. A spectrometer as claimed in claim 1, wherein the ion mobility section includes at least one of: a ring guide including a plurality of rings arranged spaced apart and around the axis thereof; a multipole rod set comprising a plurality of rods arranged around the axis thereof; and a conductive cylinder with the axis of the ion mobility section extending down the axis of the cylinder.

5. A spectrometer as claimed in claim 4, wherein the RF ion guide comprises at least one of: a ring guide including a plurality of rings arranged spaced apart and around the axis of the RF ion guide; and a multipole rod set comprising a plurality of rods arranged around the axis of the RF ion guide.

6. A spectrometer as claimed in claim 4 or 5, wherein the RF ion guide comprises a multipole rod set arranged around the axis thereof and wherein each rod comprises a plurality of rod segments, and wherein the ion focusing section includes a power supply for a DC voltage, connected to the rod segments, for supplying different DC voltages to the rod segments, thereby to generate the DC field and a potential gradient along the axis of the rod set.

7. A spectrometer as claimed in claim 6, wherein the power supply is switchable to supply voltages to the rod segments whereby a plurality of potential wells are formed.

8. A spectrometer as claimed in claim 1, 2, 3, 4 or 5, which includes means for forming a DC field and a potential gradient along the axis of the ion focusing section, said means comprising one at auxiliary elements located around the rod set and connected to a power supply for generating the DC field and the potential gradient; a multipole rod set arranged around the axis of the RF ion guide, with the rods of the multipole rod set having inclined surfaces whereby a potential gradient can be formed.

9. A spectrometer as claimed in any one of claims 1 to 5, wherein said means for maintaining a gas pressure maintains a pressure of approximately 760 Torr in the ion mobility section.

10. A spectrometer as claimed in any one of claims 1 to 5, which includes an ion source comprising one at an electrospray ion source and a MALDI source.

11. An apparatus as claimed in claim 1, wherein the ion mobility section includes a multipole rod set provided as a plurality of rod segments axially aligned with one another, a first voltage supply means connected to the rod segments for supplying an RF voltage, for focusing ions, and a second voltage supply for supplying DC voltages, connected to the rod segments for generating, in use, a potential gradient through the ion mobility section.

12. An apparatus as claimed in claim 11, wherein the final mass analysis section comprises a time-of-flight mass analyzer.

13. An apparatus as claimed in any one of claims 1 to 5, which includes a first mass analysis section and a collision cell provided between the ion focusing section and the final mass analysis section.

14. An apparatus as claimed in claim 13, wherein the first mass analysis section comprises a quadrupole mass analyzer and wherein the collision cell includes a quadrupole rod set.

15. An apparatus as claimed in claim 14, wherein the quadrupole rod set of the collision cell is provided as a plurality of rod segments, and wherein a power source is provided connected to the rod segments of the collision cell quadrupole rod set, for generating an axial DC field there along.

16. A method of separating ions based on ion mobility characteristics, the method comprising:

(i) generating ions:

(ii) providing at least one drift region having an axis extending therealong and providing and maintaining a gas at a desired pressure in the drift region;

(iii) forming a DC potential gradient along the drift region;

(iv) supplying ions to the drift region, whereby ions are driven through the drift region by the potential gradient and ions tend to separate due to differing ion mobility characteristics:

(v) passing the ions through an RF ion guide and maintaining gas at a pressure in the RF guide sufficient to focus the ions along an axis of the RF ion guide: and (vi) passing ions into a mass analyzer for mass analysis in dependence upon ion mass-to-charge ratios.

17. A method as claimed in claim 16, which includes adjusting parameters of at least one of the mass analyzer and the drift region to follow changes in properties of the ions eluting from the drift region.

18. A method as claimed in claim 17, which includes separating ions into groups of ions in step (iv) in dependence upon ion mobility characteristics, and sequentially analyzing each group of ions in step (Vi).

19. A method as claimed in claim 16, 17 or 18, which includes mass analyzing the ions in step (vi), with a time-of-flight mass spectrometer.

20. A method as claimed in claim 18, which includes establishing for each group of ions an approximate range of mass-to-charge ratios present in the, group, and mass analyzing the ions in step (vi) in a Time-of-Flight mass analyzer, and setting timing of the Time-of-Flight mass analyzer in dependence upon the range of mass-To-Charge ratios present in each group, thereby to enhance the sensitivity of mass analysis in the Time-of-Flight mass analyzer.

21. A method as claimed in claim 18 or 20, wherein all of the groups of ions together encompass all of the ions eluting from the ion mobility section within a desired range of mass-to-charge ratios.

22. A method as claimed in any one of claim 16, 17, 18 or 20, which includes, for step (v), passing ions from the drift region into a multipole rod set, providing the RF ion guides and providing an RF signal to the multipole rod set, to cool and focus the ions along an axis of the rod set, wherein the method further comprises adjusting at least one of the frequency and the amplitude of the RF to follow variations in mass-to-charge ratios of ions eluting from the drift region.

23. A method as claimed in claim 16, which includes, between steps (v) and (vi), passing the ions through a collision cell to promote formation of product ions; by one of fragmentation and reaction, and subsequently mass analyzing the product ions in step (v).

24. A method as claimed in claim 23, which includes, before passing ions into the collision cell, subjecting the ions to an upstream mass analysis step, to select a desired precursor ion for said at least one of fragmentation and reaction, and periodically resetting the precursor ion selected in said upstream mass analysis step, as different ions elute from the RF ion guide in step (iv), thereby to increase usage of ions from a sample.

25. A method as claimed in claim 16, 17 or 18, which includes controlling flow of ions from the ion mobility spectrometer with a gate, and adjusting the potential on the gate to either permit passage of ions or prevent passage of ions.

26. A method as claimed in claim 16, which includes providing the RF ion guide as a multipole rod set comprising a plurality of rod segments providing different DC potentials to axially spaced rod segments, and the method further comprising:
 (a) receiving ions from the drift region and initially applying a uniform potential gradient along the rod set;
 (b) after ions are uniformly distributed along the length of the rod set according to their mobility, establishing a potential well structure to retain groups of ions in separate potential wells; and
 (c) releasing ions separately from each potential w II for subsequent mass analysis.

27. A method as claimed in claim 26, which includes providing all or part of the drift region within the multipole rod set.

28. A method as claimed in claim 26 or 27, which includes reducing the gas pressure after establishing the potential wells, to increase ion life time in the potential wells.

29. A spectrometer comprising: an ion mobility spectrometer device, for use on promoting separation of ions based on different mobility characteristics, the ion mobility spectrometer device comprising
 an inlet for ions;
 a drift region;
 means for forming a DC field along the drift region, to generate a potential gradient along the drift region: and means for maintaining a gas pressure within the drift region, whereby ions traveling through the drift region under the influence of a potential gradient are subject to collision with a gas, promoting separation based on differing ion mobility characteristics;
 a collision cell connected to the ion mobility spectrometer for receiving ions therefrom and including a gas therein, for promoting at least one of fragmentation of ions and reaction of the ions with ambient gas, to form product ions;
 an RF ion guide having an axis, and means for supplying an RF voltage to the RF guide, to generate a field to promote focusing of ions along the axis of the RF ion guide, and
 a final mass analysis section for analyzing the product ions received from the RF ion guide.

30. A spectrometer as claimed in claim 29, which includes a first, mass analysis section between the ion mobility spectrometer and the collision cell, whereby the final mass analysis section comprises a second mass analysis section.

31. A spectrometer as claimed in claim 30, wherein the RF ion guide comprises at least one of:
 (i) a ring guide section comprising a plurality of axially aligned rings a power supply connected to the rings for generating the DC field within the drift region, the means for supplying an RF voltage being connected to the rings;
 (ii) a multipole rod set including means for establishing a potential gradient along th rod s t, the means for supplying an RF voltage being connected to the rod set; and
 (iii) a conductive cylinder.

32. A spectrometer as claimed in claim 29, 30 or 31 wherein the collision cell includes at least one at a segmented multipole rod set and means for applying varying DC voltages to the multipole rod set, Thereby to generate a DC field within the rod set and a potential gradient along the collision cell, to promote travel of ions through the collision cell; and a ring guide comprising a plurality of rings, the collision cell further including an RF power supply for the multipole rod set and the ring guide.

33. A method for separating ions based on ion mobility characteristics, the method comprising:
 (i) generating ions;
 (ii) providing a drift region having an axis extending there along;
 (iii) forming a DC gradient along the drift region;
 (iv) supplying ions to the drift region, whereby ions are driven through the drift region by the potential gradient, thereby to promote ion separation due to differing ion mobility characteristics;
 (v) passing the ions into a collision cell to promote at least one of fragmentation and reaction with a collision gas, thereby to generate product ions;
 (vi) passing the ions through an RF ion guide and maintaining gas at a pressure in the RF guide sufficient to focus the ions along an axis of the RF ion guide; and
 (vii) subjecting the product ions to mass analysis.

34. A method as claimed in claim 33, which includes, before step (v), passing the ions through a first mass analyzer, to select a desired precursor ion.

35. A method as claimed in claim 33 or 34, which includes providing a potential gradient along the collision cell, to promote passage of ions through the collision cell.

36. A method as claimed in claim 34, which includes at least one of: varying the potential gradient along the drift region with respect to time, thereby to vary the rate at which ions elute from the drift region; and
 providing a non-linear potential gradient along the drift region, whereby the potential gradient at an end of the drift region promotes elution of ions at a desired rate.

37. A method as claimed in claim 36, which includes, as different ions elute from the IMS drift region, switching the precursor ions selected by the first mass analyzer to correspond to an ion peak eluting from the drift region, thereby to maximize utilization of ions from a sample and enable sequential analysis of a plurality of different precursor ions present in the sample.

38. A method of separating ions based on ion mobility characteristics, the method comprising:
 (i) generating ions;
 (ii) providing at least one drift region having an axis extending therealong and providing and maintaining a gas at a desired pressure in the drift region;

(iii) forming a DC potential gradient along the drift region;
(iv) supplying ions to the drift region, whereby ions are driven through the drift region by the potential gradient and ions tend to separate due to differing ion mobility characteristics;
(v) passing ions into a mass analyzer for mass analysis in dependence upon ion mass-to-charge rations; and
(vi) adjusting parameters of the mass analyzer to follow changes in properties of ions eluting from the drift region.

39. A method as claimed in claim 38, which includes separating ions into groups of ions in step (iv) in dependence upon mobility characteristics, and sequentially analyzing each group of ions in step (v).

40. A method as claimed in claim 38 or 39, which includes mass analyzing the ions in step (v), with a time-of-flight mass spectrometer.

41. A method as claimed in claim 33, which includes at least one of:
varying the potential gradient along the drift region with respect to time, thereby to vary the rate at which ions elute from the drift region; and providing a non-linear potential gradient along the drift region, whereby the potential gradient at an end of the drift region promotes elution of ions at a desired rate.

42. A method as claimed in claim 33 wherein the ion undergo steps (v) and (vi) concurrenty.

43. A spectrometer as claimed in claim 29 wherein the collision cell comprises the RF ion guide.

* * * * *